(12) United States Patent
He et al.

(10) Patent No.: US 7,390,463 B2
(45) Date of Patent: Jun. 24, 2008

(54) MICROCOLUMN-BASED, HIGH-THROUGHPUT MICROFLUIDIC DEVICE

(75) Inventors: Lin He, Horseheads, NY (US); Jinlin Peng, Painted Post, NY (US); Youchun Shi, Horseheads, NY (US); Brian L. Webb, Painted Post, NY (US); Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 665 days.

(21) Appl. No.: 10/155,540

(22) Filed: May 24, 2002

(65) Prior Publication Data

US 2003/0049862 A1 Mar. 13, 2003

Related U.S. Application Data

(60) Provisional application No. 60/317,660, filed on Sep. 7, 2001.

(51) Int. Cl.
*B01L 3/00* (2006.01)

(52) U.S. Cl. .................. 422/102; 422/100; 422/101; 422/82.01; 422/82.11; 435/288.4; 435/288.5; 435/305.1

(58) Field of Classification Search .......... 422/100, 422/101, 102, 82.01, 82.11; 435/287.1, 287.2, 435/287.7, 287.9, 288.3, 288.7, 288.4, 288.5, 435/305.1, 305.3, 305.2
See application file for complete search history.

(56) References Cited

U.S. PATENT DOCUMENTS 5,302,515 A * 4/1994 Goodwin, Jr. ............... 435/29

| 5,529,756 A | 6/1996 | Brennan ............... 422/131 |
|---|---|---|
| 5,560,811 A | 10/1996 | Briggs et al. ............... 204/451 |
| 5,795,748 A | 8/1998 | Cottingham ............... 435/91.2 |
| 6,022,700 A | 2/2000 | Monks et al. ............... 435/30 |
| 6,063,633 A * | 5/2000 | Willson, III ............... 436/37 |
| 6,103,479 A | 8/2000 | Taylor ............... 435/7.2 |
| 6,108,463 A * | 8/2000 | Herron et al. ............... 385/12 |
| 6,368,865 B1 * | 4/2002 | Dahl et al. ............... 436/37 |
| 6,379,625 B1 * | 4/2002 | Zuk, Jr. ............... 422/101 |
| 2004/0239044 A1 | 12/2004 | Blatter et al. ............... 277/602 |

FOREIGN PATENT DOCUMENTS

| CA | 2459241 | 4/2003 |
| EP | 0 678 745 | 7/1998 |
| WO | WO 00/05336 | 2/2000 |
| WO | WO 00/45950 | 8/2000 |
| WO | WO00/67907 | 11/2000 |
| WO | WO 01/19517 | 3/2001 |
| WO | WO 02/34197 | 5/2002 |
| WO | WO 03/022421 | 3/2003 |

* cited by examiner

*Primary Examiner*—Jan M Ludlow
(74) *Attorney, Agent, or Firm*—Tina N. Thompson; Thomas R. Beall

(57) ABSTRACT

A biological assay device for use in molecular biology, pharmaceutical research, genomic analysis, combinatorial chemistry, and in the general field of the analysis of molecules that may be deposited on supports of various kinds is provided. Specifically, the present invention includes a fluidic or microfluidic device, which integrates fluidic capability into existing multi-well plates of standard configuration, for performing either single or continuous fluidic manipulations in a high-throughout format. Methods for the use and manufacture of these devices are also provided.

20 Claims, 19 Drawing Sheets

FIG. 12A  4-HR. HYBRIDIZATION WITHOUT FLUIDIC MOVEMENT
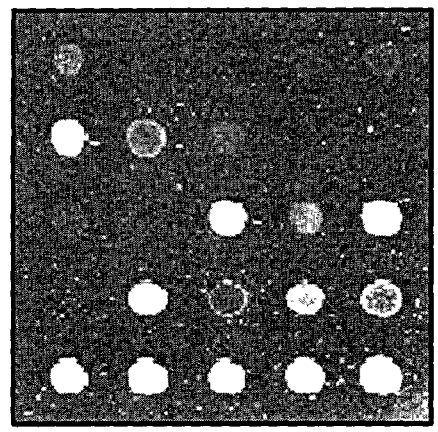
FIG. 12B  4-HR. HYBRIDIZATION WITH FLUIDIC MOVEMENT
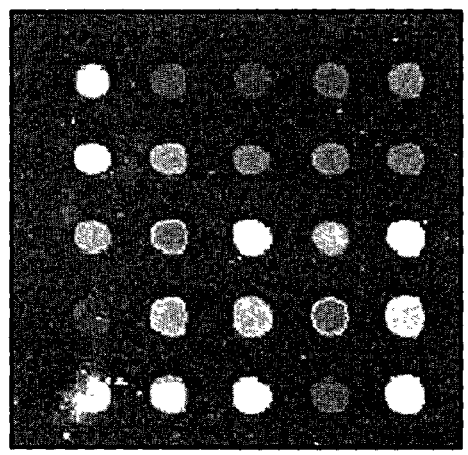

MICROCOLUMN-BASED, HIGH-THROUGHPUT MICROFLUIDIC DEVICE

RELATED APPLICATION

The present Application is related to U.S. Provisional Patent Application No. 60/317,660, filed on Sep. 7, 2001.

TECHNICAL FIELD OF THE INVENTION

The present invention relates to the field of high-throughput biological assay devices for use in molecular biology, pharmaceutical research, genomic analysis, combinatorial chemistry, and in the general field of the analysis of molecules that may be deposited on supports of various kinds. Specifically, the present invention includes a device for performing microfluidic manipulations in standard-configuration multiwell plates.

BACKGROUND OF THE INVENTION

Manipulation of biological and/or chemical molecules in solution has become an essential aspect of various kinds of analysis. For instance, in biomedical or pharmaceutical assays, cellular components, proteins or nucleic acid (DNA) molecules are studied to ascertain particular genetic risk factors for disease or the efficacy of drug trials. Recently, a class of sample-receiving substrates has been developed for "microfluidic" bioassay devices, popularly called "lab-on-a-chip" devices. Lab-on-a-chip technology is exciting the interest of scientists in many areas. This technology can be used to carry out biological and clinical analyses, to perform combinatorial chemistry, and to carry out full-scale analyses from sample introduction to chemical separation and detection, on a single, miniaturized device efficiently and economically. Hence, microfluidic devices have recently gained great appeal in the biomedical, genomic, and pharmaceutical industries, where they offer the benefits for miniaturization, integration and automation. Substrates of these devices are integrated microfluidic assay systems with networks of chambers connected by channels, which have microscale dimensions, typically on the order of between 0.1 µm and 500 µm. These channels allow the movement of small volumes of reagent to assay stations. Such microfluidic substrates may be fabricated using photolithographic techniques similar to those used in the semi-conductor industry, and the resulting devices can be used to perform a variety of sophisticated chemical and biological analytical techniques.

Because of the variety of analytical techniques and potentially complex sample flow patterns that may be incorporated into particular microfluidic test substrates, significant demands may be placed on the analytical units, which support the test substrates. The analytical units not only have to manage the direction and timing of flow through the network of channels and reservoirs on the substrate, they may also have to provide one or more physical interactions with the samples at locations distributed around the substrate, including heating, cooling, exposure to light or other radiation, detection of light or other radiation or other emissions, measuring electrical/electrochemical signals, pH, and the like. The flow control management may also comprise a variety of interactions, including the patterned application of voltage, current, or power to the substrate (for electrokinetic flow control), or the application of pressure, vacuum, acoustic energy or other mechanical interventions for otherwise inducing flow.

As a consequence, a virtually infinite number of specific test formats may be incorporated into microfluidic test substrates. Because of such variety and complexity, many if not most of the test substrates will require specifically configured analyzers in order to perform a particular test. It is indeed possible that particular test substrates use more than one analyzer for performing different tests. The need to provide one dedicated analyzer for every substrate and test, however, will significantly reduce the flexibility and cost advantages of the microfluidic systems. Additionally, for a specifically configured analyzer, test substrates are generally only useful for performing a limited number of assay formats and functions. As the complexity and costs of test substrates increase, it becomes more desirable to increase the number of useful assay formats and functions for a particular test substrate-analyzer combination, or for a particular class of substrates in combination with a specifically configured analyzer.

For all their virtues, most current lab-on-a-chip devices, however, are inherently low throughput, allowing for only a small number of samples to be assayed at a time. Current microfluidic devices are limited typically to less than 40 or 50 assays per chip. Further, they are rather cumbersome to handle since they do not conform to standard robotics and often require manual processing. Therefore, it would be desirable to provide a high throughput microfluidic device that is configured to work with equipment for bio-chemical-genomic assays of an industry-standard format. Thus, as an aspect of the present invention, the device provides high-throughput microfluidic processing that is compatible with standard microtiter plate formats.

SUMMARY OF THE INVENTION

The present invention pertains to a fluidic or microfluidic device, which integrates fluidic capability into existing multiwell plates of standard configuration, for performing either single or continuous fluidic manipulations in a high-throughout format. The device includes a number of fluidic modules extending at an angle, preferably orthogonal, from a support structure or plate. Each fluidic module is three-dimensional, has a major surface located remotely from the support structure, and at least one sidewall between the major surface and the support structure. Unlike current technologies that position fluidic channels in the fluidic substrate or plate itself, the present invention locates fluidic channels in each of the fluidic modules. Each of the fluidic modules can be inserted into an individual well of a microplate. This design brings high-throughput microfluidic capabilities to microplates of standard configuration without modification of the conventional microplate design, as it has been a frequent necessity with current microfluidic systems. This feature permits the invention to work with current robotic handlers and analysis, imaging or reading technologies.

In addition to the advantages already mentioned, the present invention has several other virtues. Not only is the present invention compatible with existing well plates but also solves the problems associated with evaporation and mixing without the need to modify existing 96-well plates. A capillary space is formed between the bottom surface of a well of a microplate and the fluidic module. By adjusting the capillary space between the top surface of each fluidic module and the bottom wall of the respective well, one can easily regulate the amount of space available to accommodate more or less volume of assay solution. Once inserted into a well, the fluidic module can function like a cover-slip on a conventional flat slide, which can overcome evaporation problems and prevent the sample from drying out.

Furthermore, the present invention has a capability for continuous fluidic movement. The arrangement of the fluidic channels in each fluidic module permits one to supply a continuous flow of fresh reagents and solutions into each microplate well. Continuous fluidic movement is useful for such functions as mixing, flow-through washes or filtration, as well as real-time assay interactions. For instance, using the fluidic modules, one may perform multi-analyte assays on porous substrates with continuous flow-through. To transport and mix fluidic samples, in some embodiments, a set of at least first and second microchannels, each with inlet and outlet ports, runs through the body of each fluidic module. By means of an automated pumping system or a manual pipette through the fluidic network, an interface for mixing fluidic samples may easily be created inside the zone or chamber defined by the top surface of the fluidic module and the bottom of the well. Moreover, microfluidic analytical technology has a number of advantages, including the ability to use very small sample sizes.

While employing small volumes of assay solution, the present fluidic device can significantly improve binding (e.g., hybridization) efficiency for arrays of analytes, which may be contained on the surface of the microcolumns. Further, an electrochemical sensor or a biosensor with gratings or optical waveguides is include for real-time monitoring (e.g., pH, binding or dissociation) of reactions on the remote surface of each microcolumn or in the microplate well.

In another aspect, the present invention relates to a method of using the fluidic device with a microplate. The method includes providing a fluidic device, according to the present invention, and analytes on either the remote major surface of each fluidic module or a bottom wall surface of a well in the microplate. The fluidic modules can be formatted to perform numerous specific analytical operations including mixing, dispensing, reacting, and detecting.

Other features and advantages of the present device will become evident from the following detailed description. It is understood that both the foregoing general description and the following detailed description and examples are merely representative of the invention, and are intended to provide an overview for understanding the invention as claimed.

BRIEF DESCRIPTION OF THE DRAWINGS

FIG. 12 shows a comparison of two nucleic acid arrays. Hybridization on the array on the left was performed under conventional, static fluidic conditions. The array on the right was preformed using a fluidic device according to the present device.

DETAILED DESCRIPTION OF THE INVENTION

Figure 1:
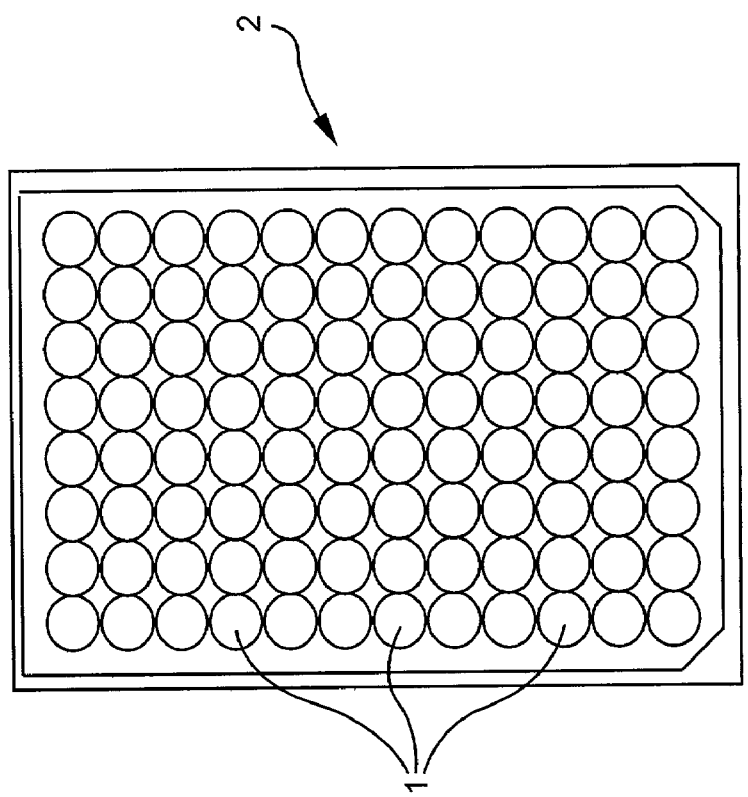
FIG. 1 is a diagram showing a top view of a standard 96-well plate.

The current gold standard in high-throughput, bio-chemical assay devices is the 96-well microplate as illustrated in FIG. 1. Conventional technologies used to miniaturize assay volumes in multi-well microplates have met with a range of problems associated principally with evaporation. Also, conventional microplates often give imprecise test results due to poorly controlled fluidic mixing. Efforts to solve the evaporation and poor mixing problems within a 96-well plate have led others to modify the basic 96-well-plate footprint by integrating capillaries (e.g., International Patent Application No. WO 00/67907; Arteas™ microfluidic devices by Aclara Biosciences, Inc.), and/or additional wells into the plate.

Hydrostatic and surface tension forces drive fluid from an evaporation control well through a microfluidic channel to an assay well. The function of these capillaries and additional wells in the plate is either to eliminate the negative effects of evaporation by compensating for any evaporation with negligible change to sample during assay development, or to allow small volume liquid diffusional separations of biomolecules. This type of design has several inconveniences. One is that the design requires an extra set of evaporation control wells, and does not address sufficiently the problem of fluidic mixing. Further, neither of the two approaches provides for kinetic studies of reactions, where a continuous supply of reagents or sample is required. A device that can provide integrated reagent delivery, mixing, and washing in a single unit for use in a standard format microplate (e.g., 96 or 384-well, etc.) is currently unavailable. The costs for modifying the analytical and control systems interface as well as the costs required for obtaining test substrates for desired assays The present invention solves the evaporation, mixing and fluidic manipulation problems without the need of additional wells. As noted above, the present invention relates to a device for performing biological or chemical analysis, and provides a simple and convenient means of perform low-volume fluidic-integrated bioassays within standard-format microplates. This capability is a very attractive, advantageous feature of the present invention. The device makes use of a fluidic or microfluidic system that is adapted to be compatible with microplates of industry-standard matrix formats, and conforms to current robotics. In its broadest sense, as used herein, "fluid" relates to liquid or gaseous media, or both.

Figure 2:
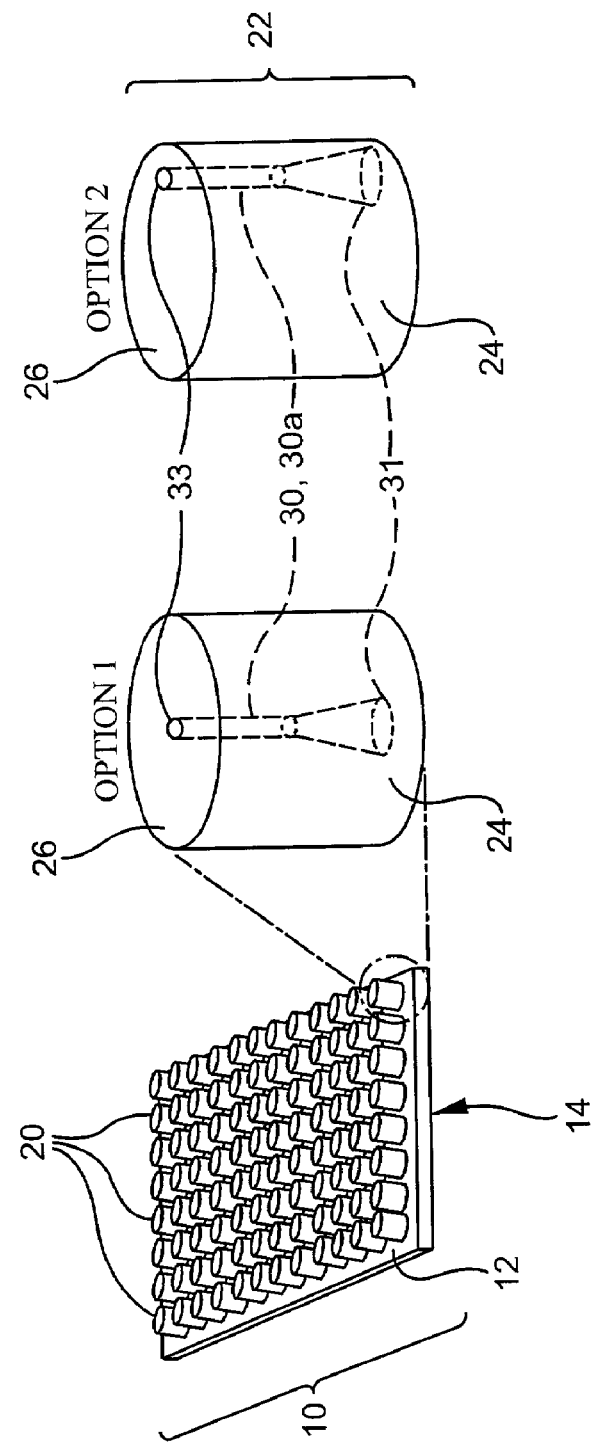
FIG. 2 shows a schematic representation of a plate of fluidic modules, according to the present invention. Each module is a microcolumn with a fluidic channel defined by an inlet and outlet port for sample transport. For illustration purposes, two different locations of the inlet and outlet are depicted.
Figure 9A:
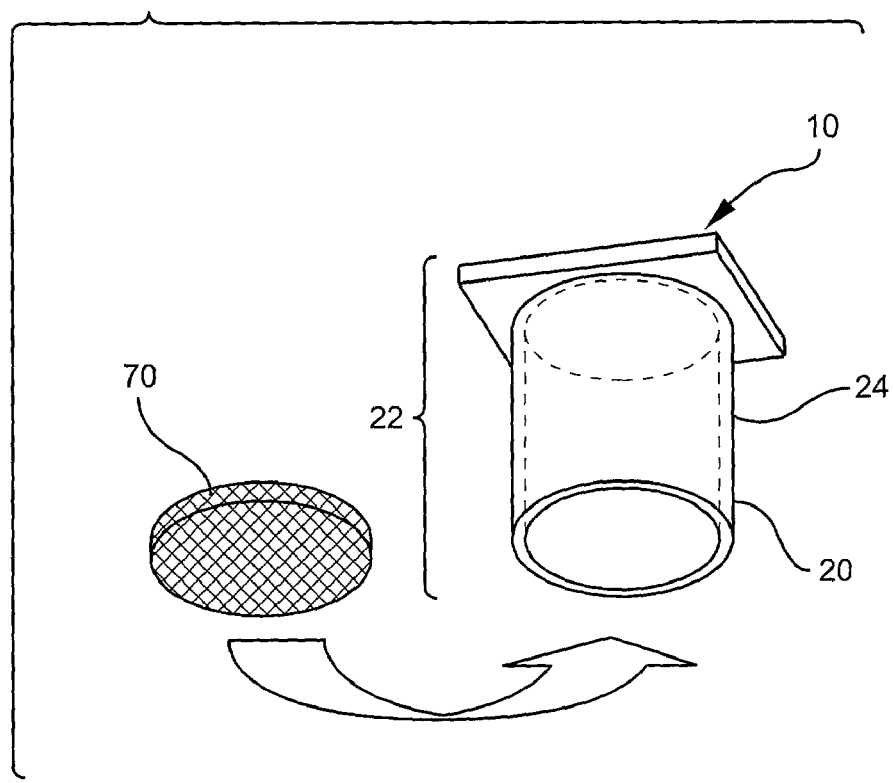
FIG. 9 depicts a schematic of a porous borosilicate disc (Pyrex®) as the top or major surface of a microcolumn according to the present invention.
Figure 9B:
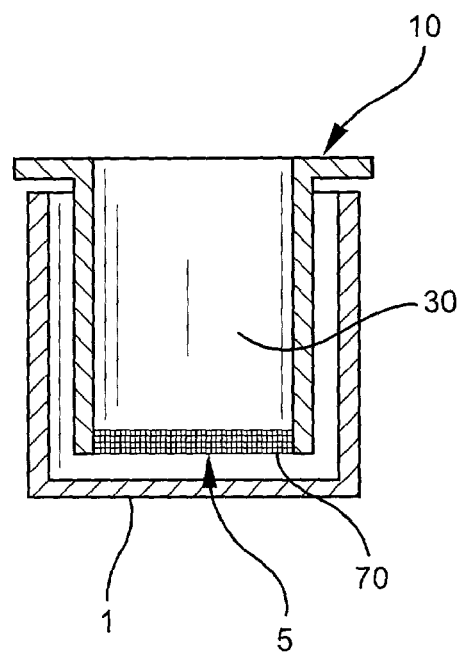
Figure 10B:
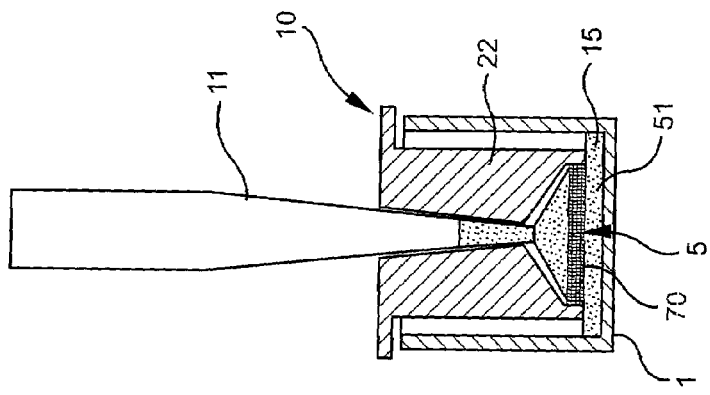
FIG. 10 depicts an array plate with 96 microcolumn in a high-throughput, flow-through configuration.
Figure 10A:
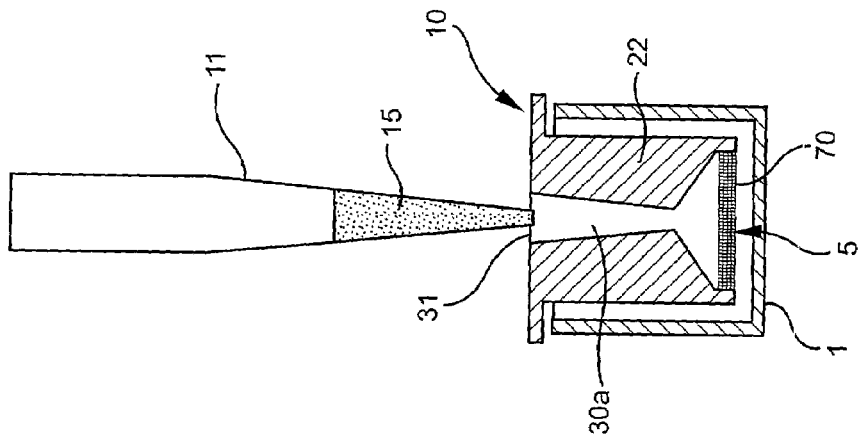
Figure 11:
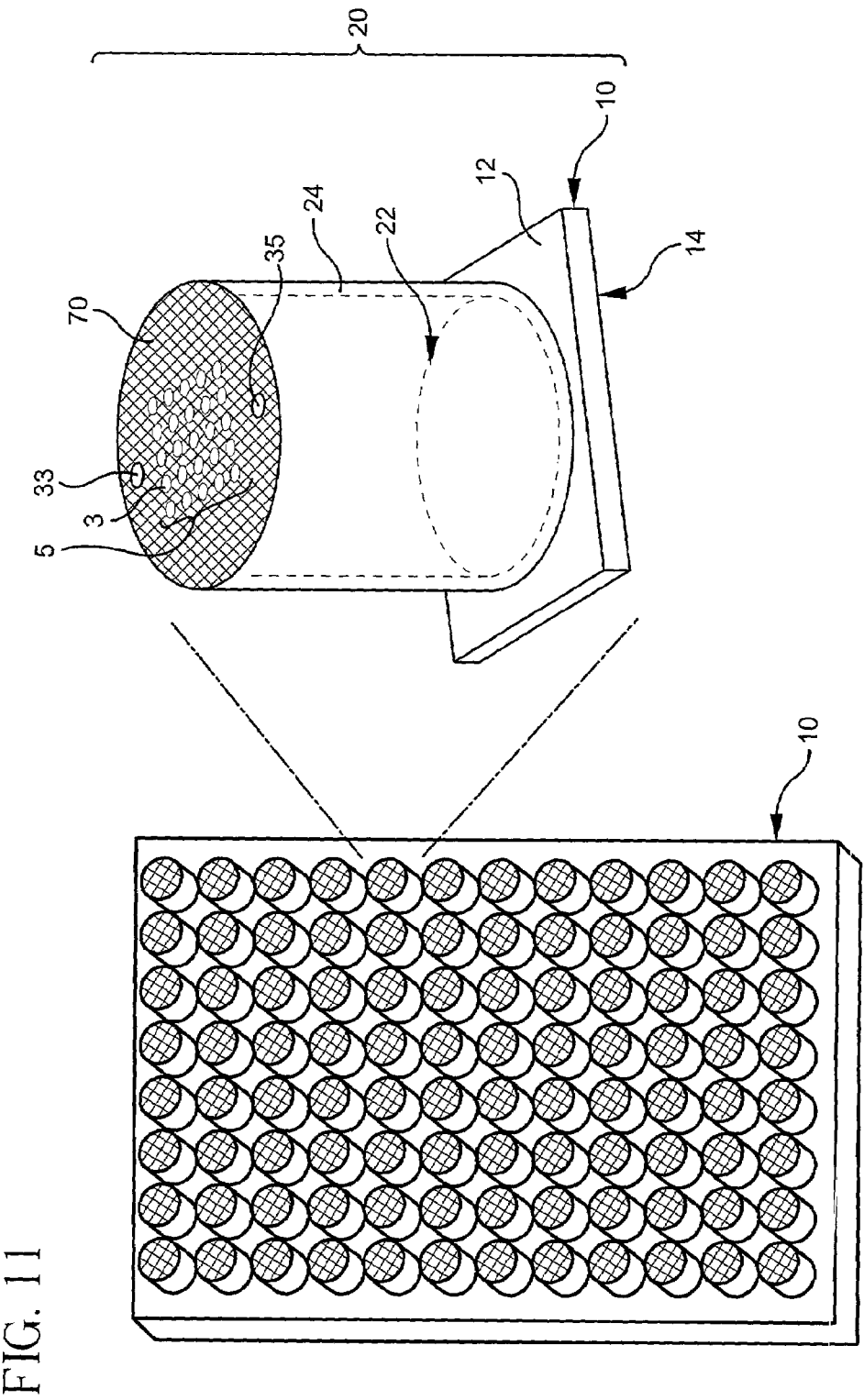
FIG. 11 illustrates a conduit-pipette-driven fluidic-module system.
Figure 13A:
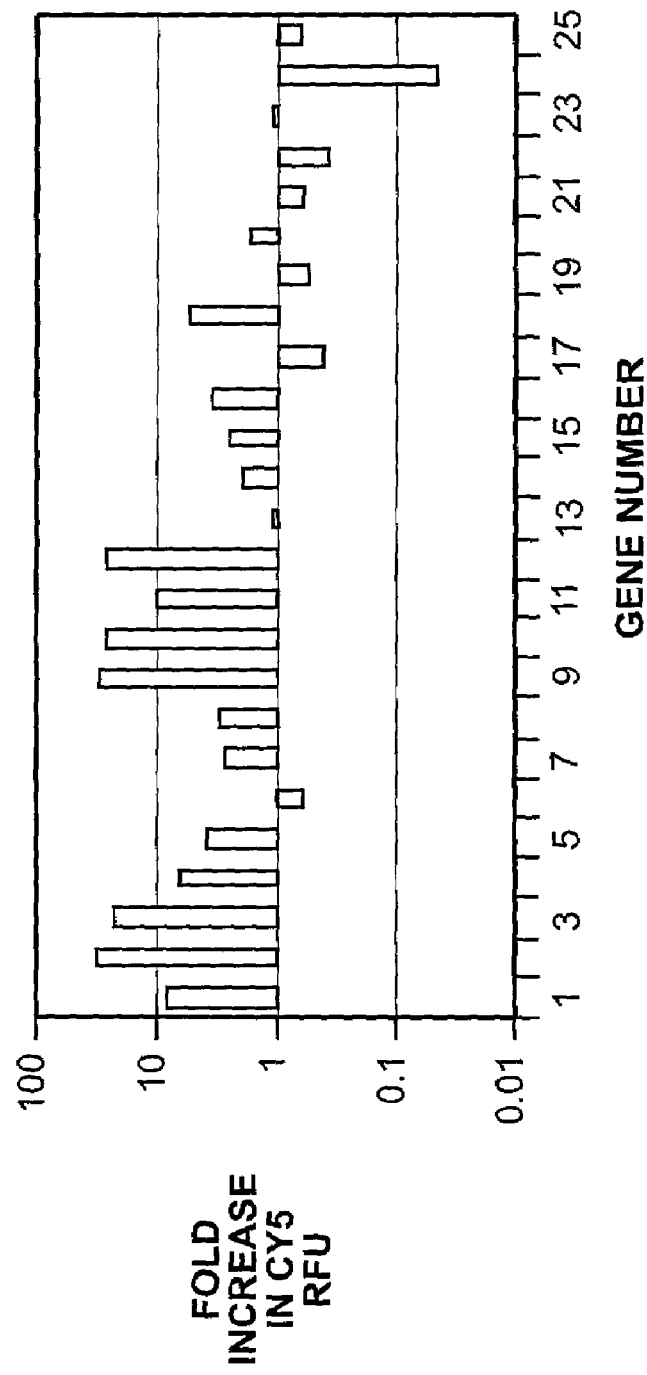
FIG. 13 present graphs A-D, which summarize the hybridization results of the arrays in FIG. 12.
Figure 13B:
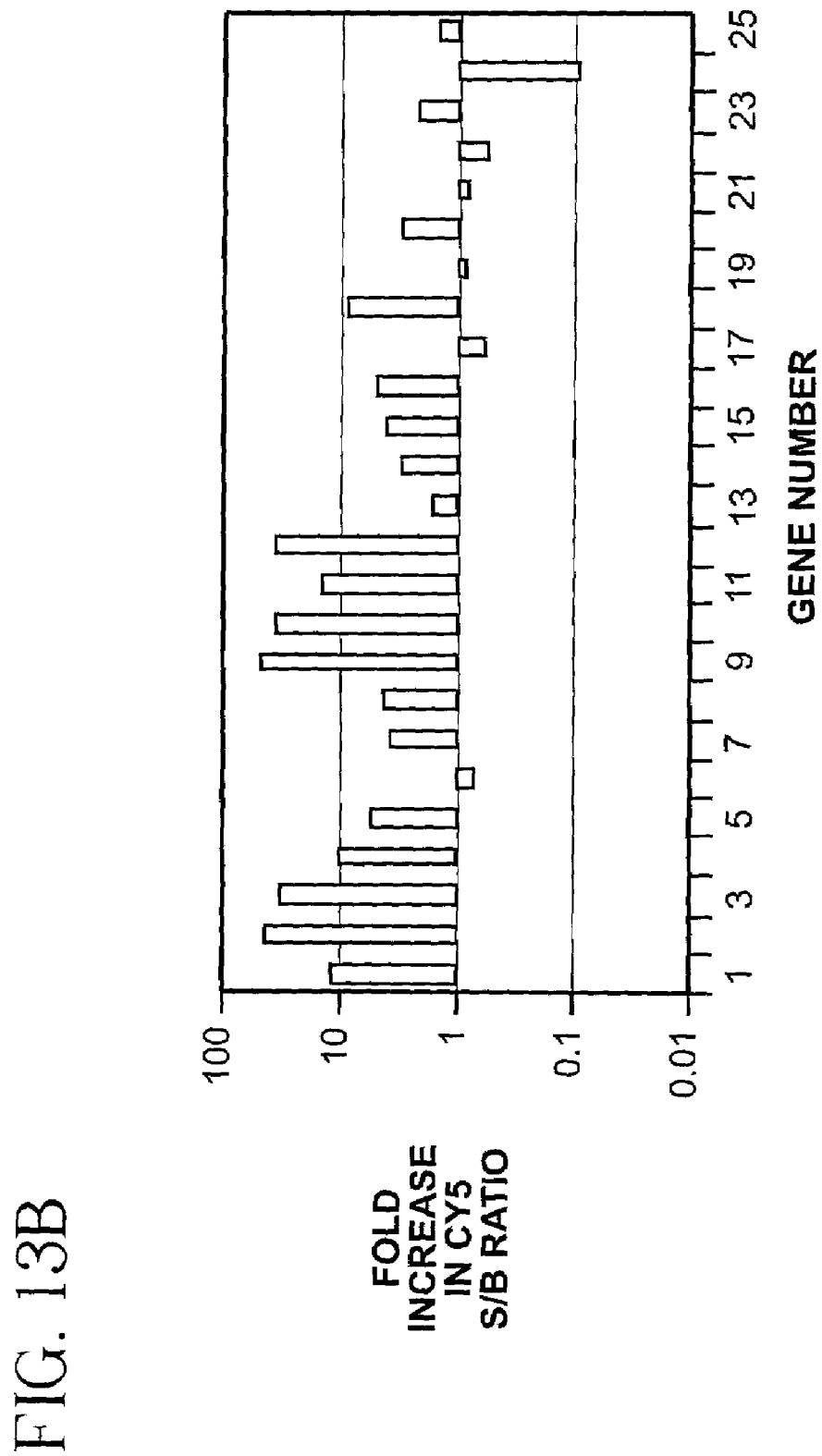
Figure 13C:
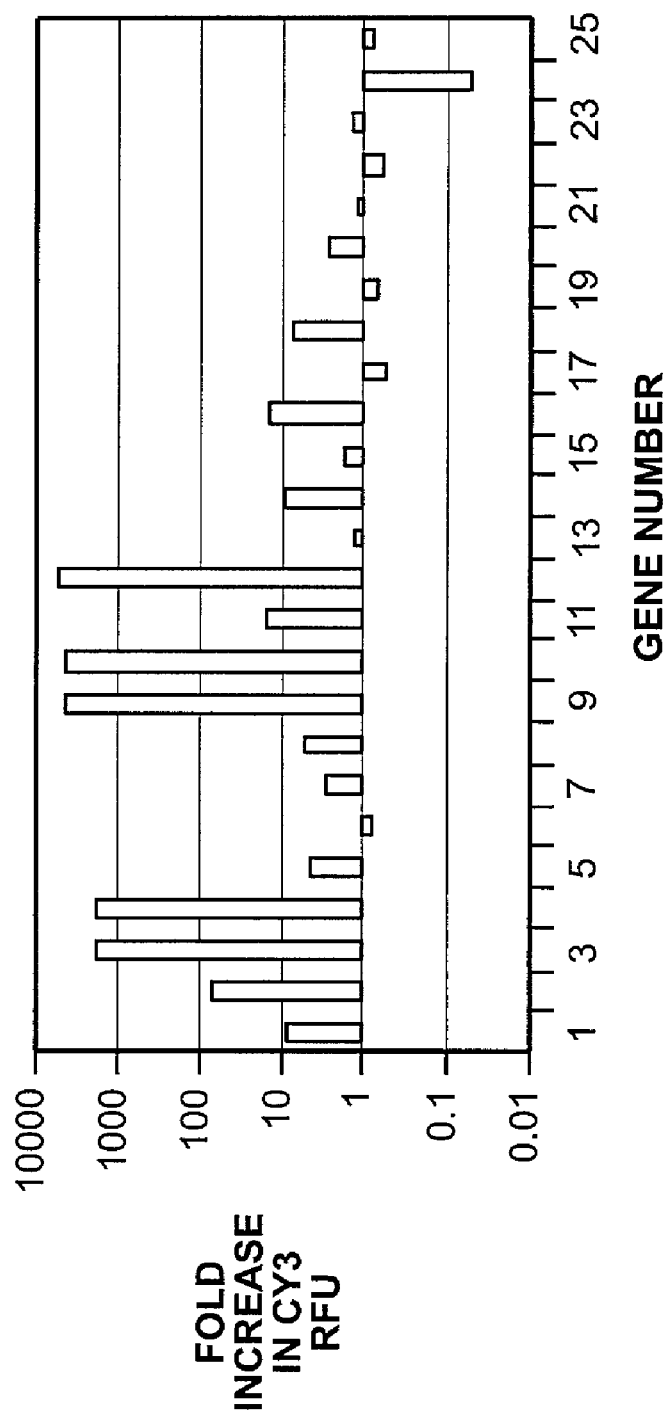
Figure 13D:
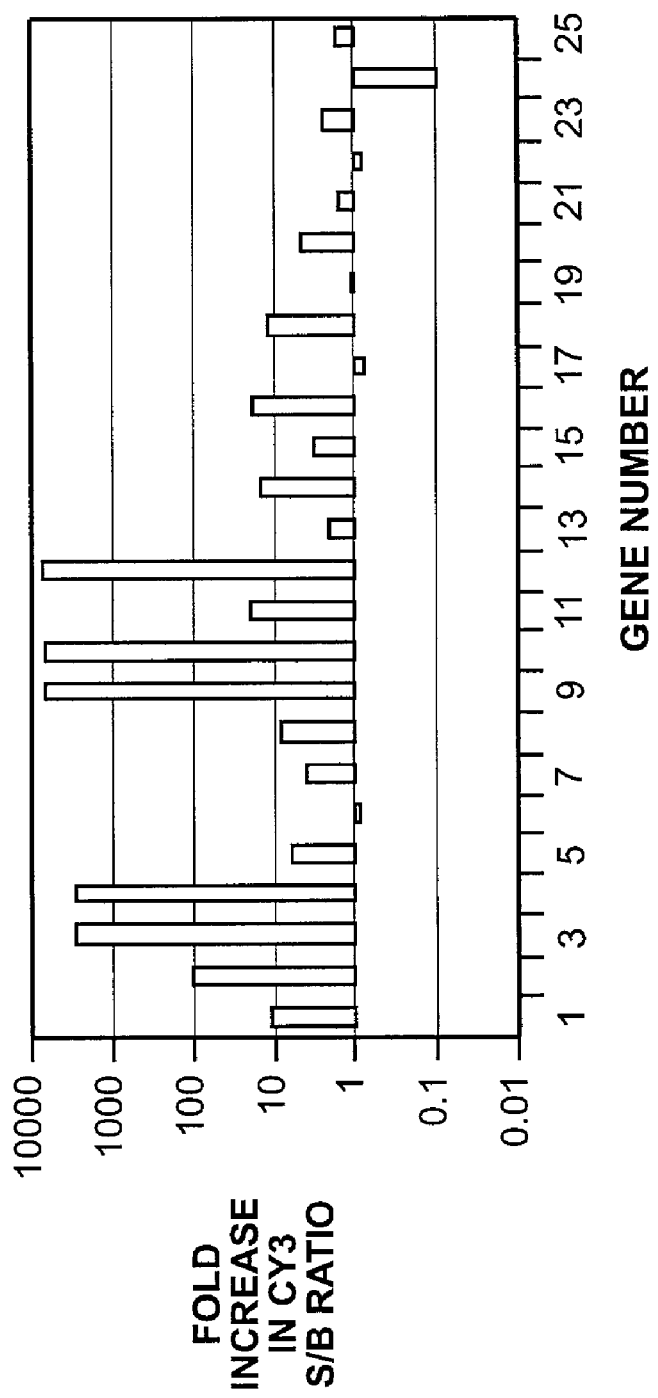

The present device is an extension and further incarnation of the so-called microcolumn or micropillar device described in U.S. Provisional Patent Application No. 60/317,660, the content of which is incorporated herein by reference. As illustrated in FIG. 2, the present device comprises a support structure or plate 10 with a first 12 and second 14 surface, a number of fluidic modules 20 extending from the first surface 12 and oriented vertically relative to the horizontal plane of the support structure 10. Each fluidic module 20, at least in part, takes the form of a three-dimensional microcolumn 22 made from polymer, glass, metal, or other suitable substrate materials. In additional to a sidewall 24, the three-dimensional microcolumn 22 has a major surface 26 remotely located relative to the first surface 12 of the plate 10 and a set of at least one hollow cavity 30 or fluidic channel 30a formed therein. According to the embodiments depicted in the accompanying figures, each fluidic module has at least a first fluidic channel. In general, the hollow cavity may have various dimensions with either a rather large or small diameter. FIGS. 2-8 present schematic drawings of various iterations of the present fluidic device with fluidic microchannels (e.g., ≦550-500 µm in diameter). Other embodiments with larger channels are shown in FIGS. 9-11, which will be discussed below.

Figure 7:
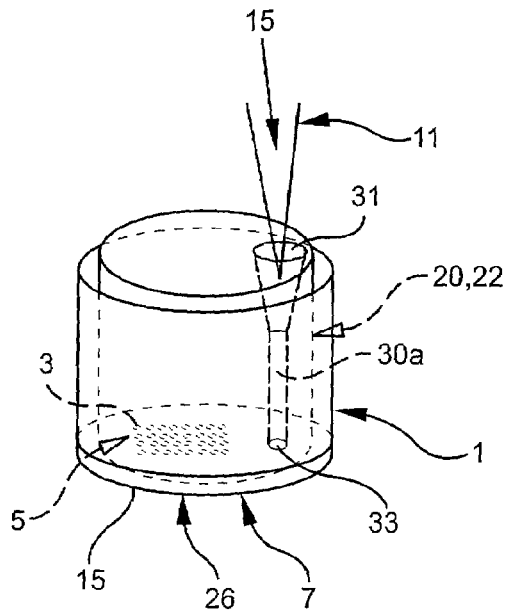
FIG. 7 illustrates an alternate embodiment of the present invention, with an array of analytes on the major, remote surface of the microcolumn, the bottom surface of the well of a microplate, or both. Reagent solution or samples can be injected through the microchannel into the well. A reaction zone is between the microcolumn and the bottom of the well.

FIG. 2 further depicts an enlarged view of a basic conception of present invention. A hollow cavity 30 extends all the way through the microcolumn 22, from the support's second surface 14 to the microcolumn's remote major surface 26. Each hollow conduit in the microcolumn 22 will have an inlet 31, outlet 33, and a fluidic microchannel 30a for transporting and mixing sample solution. Such a hollow cavity could be used as a conduit for introducing reagent or media solutions directly to the area of a well 1 located under the major surface 26 of the microcolumn 22. As represented in FIG. 7, an array 5 of biological or chemical analytes 3 may be located on either the major surface 26 of the microcolumn 22 or the bottom wall surface 7 of a microplate well 1. The biological or chemical analytes can be DNA, RNA, oligonucleotides, proteins, peptides, cells, cellular components, and small biological or chemical molecules, or drugs. FIG. 2, also shows two possible options for locating the hollow conduit, either through the center or off to a side of the microcolumn.

The present device may further include at least a second fluidic channel, which extends at least partially through either the microcolumn 22 or support structure 10 from a terminus 35 on the remote major surface 26 to a second outlet portal 37. Thus, each of the two fluidic channels in the microcolumn may have a separate inlet and outlet at their respective termini. Embodiments with two channels are depicted in the accompanying figures for simplicity of illustration. This, however, is not to be limiting of the invention, since each microcolumn may, depending on the desired use, have any number (e.g., 6, 7, or 8) of hollow conduits located around the periphery or through the center of the microcolumn.

Figure 3A:
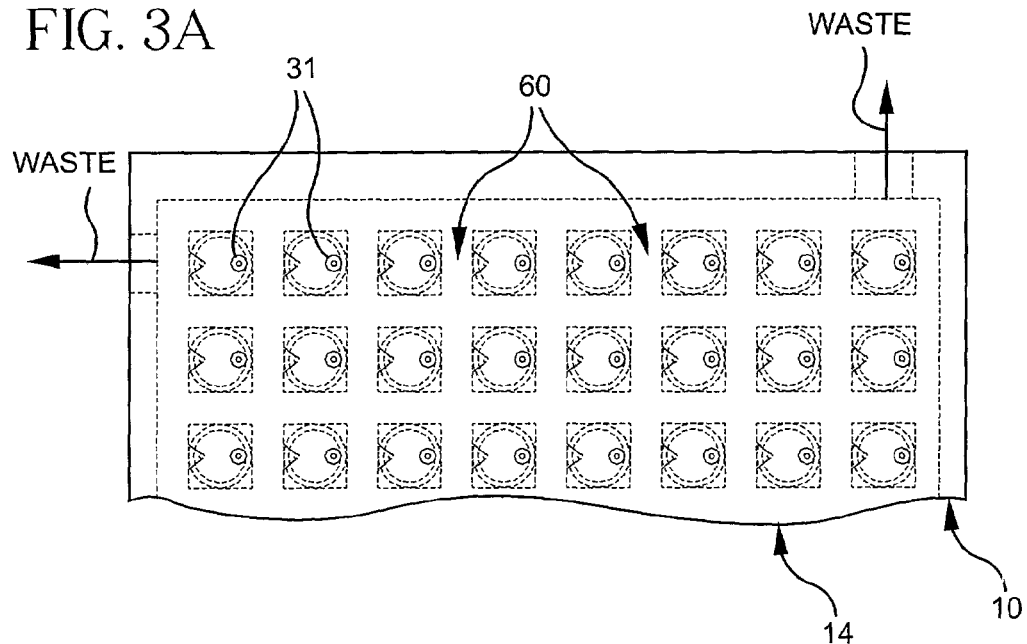
FIG. 3A is a top view of one embodiment of the present invention with fabricated waste channels on top of the substrate.
Figure 3B:
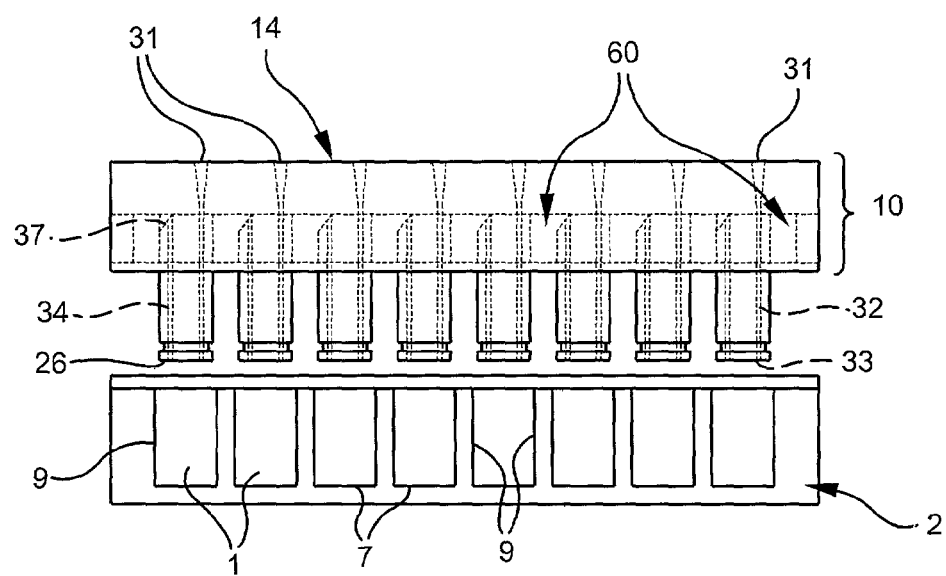
FIG. 3B is a side view of the embodiment depicted in FIG. 3A where inlets, outlets and microchannels are etched or otherwise formed through the microfluidic modules or columns, and a side view of a standard 96-well plate into which the microfluidic columns are inserted.

In an alternate embodiment, FIG. 3A shows a top-down, partial view of the second or top surface 14 of the support structure 10, also known as an upper plate when joined with a microplate 2. The embodiment has two fluidic channels 32, 34. The first fluidic channel has a first inlet port 31 located in the support structure's top surface 14 and extends through the support structure 10 and the body of the microcolumn 22 to the remote major surface 26 to a first outlet or terminus 33. In particular embodiments, each fluidic inlet 33 is offset to one side of the center of each fluidic module 20. As depicted in FIGS. 2 and 3B, the first inlet port 31 can be made to receive a pipette tip, syringe, male luer or adaptor-tip for tubing or other conduit. For this purpose, preferably, the inlet is tapered. Sample fluids can be introduced through the inlet opening into the first fluidic channel 32.

For high-throughput capacity, the fluidic modules are arrayed in a dense matrix (e.g., 96-, 192-, 384-, 576-, or 1536-well) format, although other less dense formats (e.g., 6, 8, 12, 24, or 48-well) are also contemplated as part of the present invention. As illustrated in FIGS. 2 and 3B, each fluidic module has a size and configuration, which can be introduced into a corresponding well of a microplate, and positioned a predetermined distance above a bottom wall of the corresponding well.

Figure 4A:
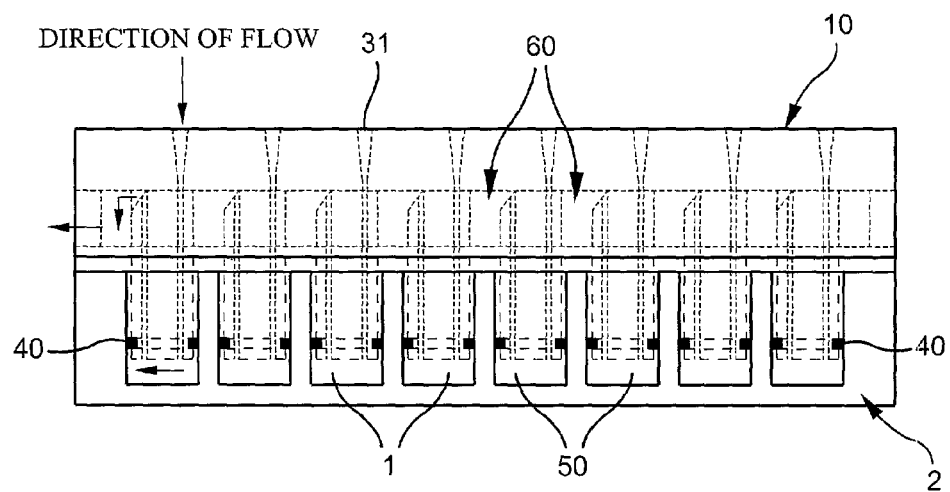
FIG. 4A is a diagram where the fluid flow direction is shown for the design of the present invention depicted in FIG. 3B.
Figure 4B:
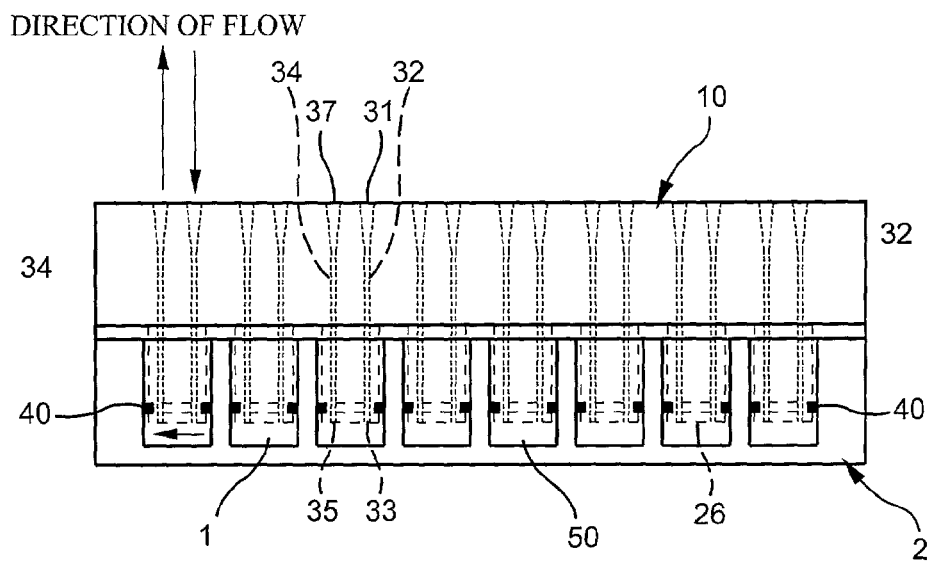
FIG. 4B is a diagram where the fluid flow direction is shown for the design of the present invention depicted in FIG. 3C.
Figure 5:
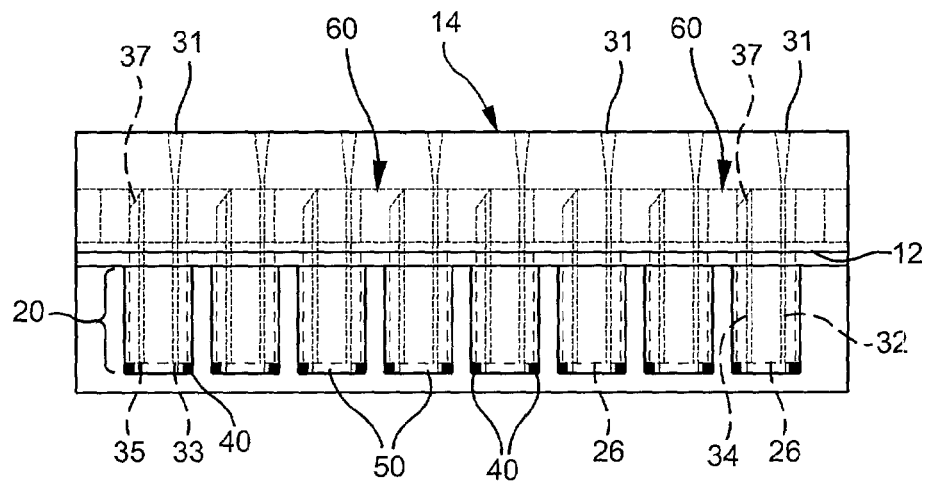
FIG. 5 is a diagram of an alternative sealing design of the present invention depicted in FIGS. 4A and 4B.

As illustrated in FIGS. 4-6, each microfluidic module 20 also has a sealing mechanism that engages with either the bottom wall or a sidewall of the well, or a top surface of the microplate, to form a fluid-tight space, which functions as a capillary-sized reaction zone or chamber. The sealing mechanism can be a variety of things, including a gasket, an O-ring, a rib or flange on the remote major surface. A niche 38 girdling the microcolumn provides a location for the sealing mechanism to attach to the device. A sealing mechanism, like an O-ring 40, on the side of the microcolumn 22, provides a gas or liquid-tight seal between the channeled microcolumns and a well 1. This will prevent assay sample or solution from wicking up a sidewall 9 and out of the microplate 2. When each microcolumn 22 is pressed into the corresponding microplate well 1, an O-ring 40 can form a sealed assay or reaction chamber 50 with microfluidic communication and access to the outside. When placed around the peripheral edge of the remote major surface 26 of the microcolumn 22, as illustrated in FIG. 5, the height of the O-ring 40 defines the height of the chamber 50 between the top surface 26 of the microcolumn and the bottom 7 of the well 1. A clamping element, not shown, also may be employed to hold the upper plate tight against the microplate beneath.

In some embodiments, the microcolumns each have a separate first 32 and second channels 34. A fluidic transfer interface for the inlets and outlets is included to convey simultaneously different samples or reagents through the microcolumns into each well of the plate. One may introduce fluid through an inlet port 31 and first fluidic channel 32 into the reaction chamber 50 and push the fluid out through the second fluidic channel 34, when additional fluid enters through the first microchannel 32. The direction of flow can also be reversed or cycled back and forth to provide fluidic agitation in certain applications. This type of configuration is conducive for performing high-throughput analysis and other uses, such as relatively large-scale combinatorial chemistry. Sample or reagent is injected, using either a standard automated pipette or valving systems with a syringe pump, through the inlet microchannel and spreads across the thin reaction zone 50a between the remote major surface of the microcolumn and the bottom wall of the well. Commercially available male luer adapters (Upchurch Scientific, Oak Harbor, Wash.) or similar components connected to tubing can be attached to the inlet.

Figure 3C:
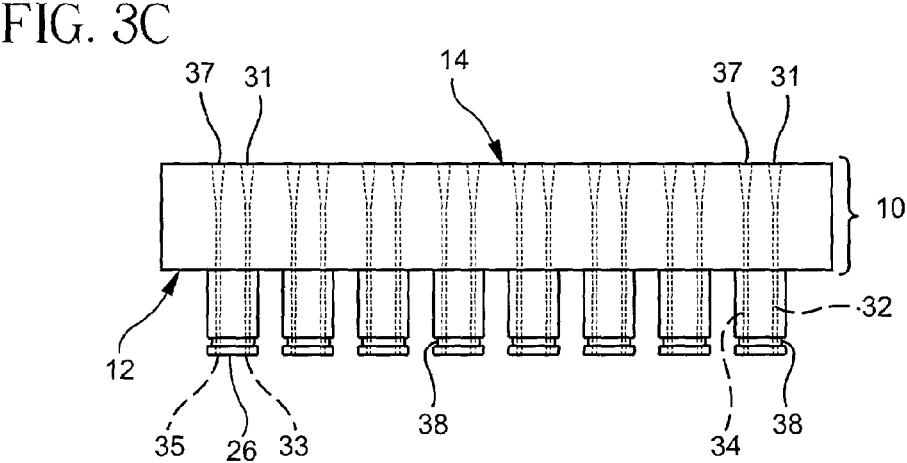
FIG. 3C is a diagram of an alternative design of the present invention.

The second microchannel 34 can be integrated to a waste solution chamber or passages 60 located within the substrate of the support structure 10, such as shown in FIG. 3B. This feature permits fluid sample to be collected when the fluidic exits from each well 1. The waste chambers 60 in the support structure may form a common reservoir or may each drain out through individual channels 62. Alternatively, as depicted in FIG. 3C, the inlet portal 35 of the second microchannel 34 may extend to an outlet port 37 that exits onto the second or top surface 14 of the support structure 10. In this situation, the second outlet port 37 is also configured to receive a conduit for fluids. For instance, using male luer adapters, separate waste tubing may be attached to the second outlet to remove sample waste or the reacted solution. By attaching the other end of such tubing to a pumping system for injecting sample and wash reagents, this configuration of fluidic channels can provide a continuous flow of fluids for certain applications.

The present fluidic system can also enhance array-based assays. Development of effective analytical tools for genomics and proteomics is very challenging. An established major assay platform is the microarray chip, which has found wide applications. One of the limitations of arrays on flat solid surfaces, however, is that hybridization efficiency (i.e., the binding of the probe molecule to its immobilized target molecule) is limited by the diffusion of the probe molecule to the target. For instance, mRNA expression profiling using DNA index arrays normally requires relatively high probe concentrations and long incubation times, from a few hours up to overnight, for efficient hybridization to occur. Sometimes slight surface difference in flatness can cause dramatic change in the hybridization results because of the different diffusion pattern.

In microarray applications, rectilinear arrays of biological or chemical materials (e.g., cDNA, oligonucleotide, and proteins) can be first deposited or printed onto either the remote, major surface of each microcolumn or the bottom wall of microplate wells, or both. Then, the plate of microfluidic modules is inverted. With remote surface facing downward, each microcolumns is inserted into a well of a microplate. An assay solution 15 can be introduced into the well 1 through the fluidic channel 30a, as shown in FIG. 7. Since the remote, major surface 26 of each microcolumn 22 covers virtually the entire reagent or sample solution 15 introduced into each well 1, the microcolumn, especially the embodiments with seals, can minimize evaporation from the well. The amount of assay mixture used can be adjusted by changing the distance (gap) between the major surface on the microcolumn and the bottom of its corresponding well. Due to the relatively close distance between the top surface and the bottom surface of the micro-titer well, surface tension and hydrostatic forces confine assay mixture to the area under the arrayed biological materials. The gap distance between the two surfaces may range from ~1-500 microns, preferably ~5-250 microns, or ~50-100-150 microns. This feature can reduce the volume of reagents required to perform an assay, localize the use of reagent solution directly on the biological materials, and stimulate microfluidic flow.

Figure 14:
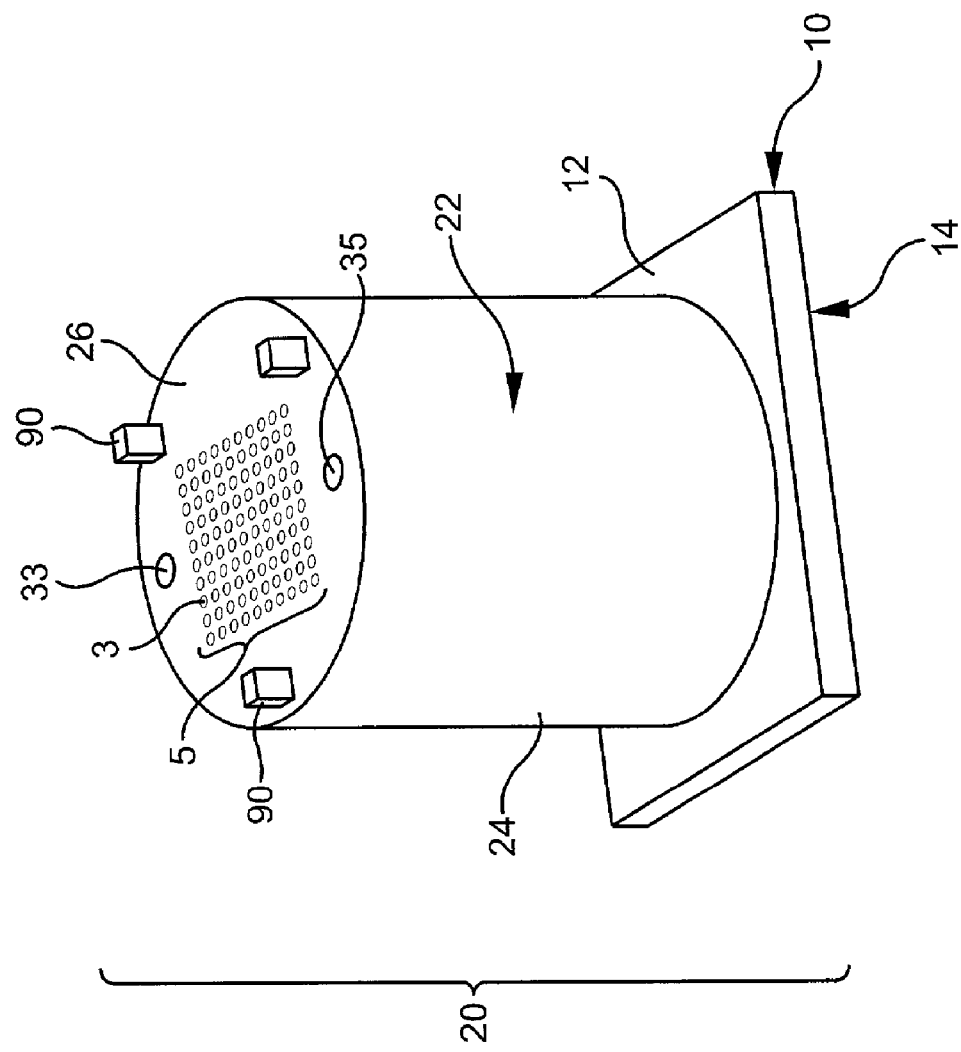
FIG. 14 is an embodiment of the present invention with one kind of spacer located along an edge of the remote surface of the microcolumn.
Figure 15B:
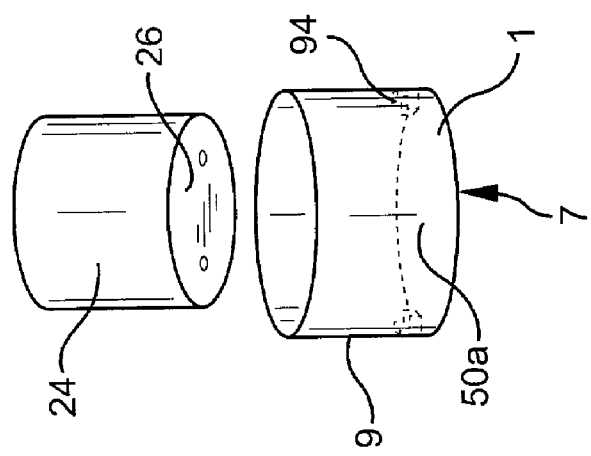
FIGS. 15B and 15C show two embodiments of flange type spacers for maintaining a constant distance for a capillary space between a remote surface of a microcolumn and the bottom surface.
Figure 15A:
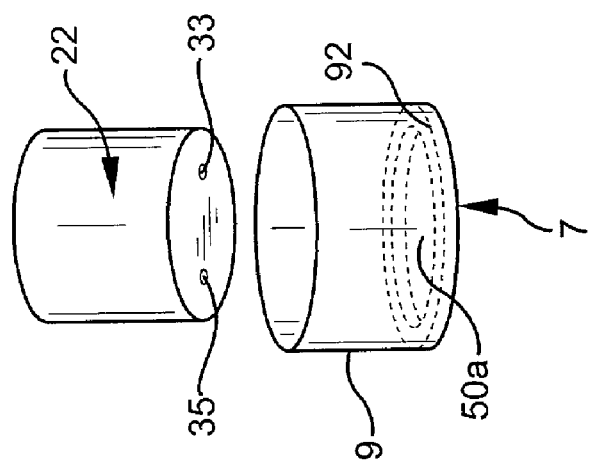
FIG. 15A shows a raised rib type spacer located around the periphery of the bottom surface of a micro-titer well, for maintaining a constant distance for a capillary space between a remote surface of a microcolumn and the bottom surface.
Figure 15D:
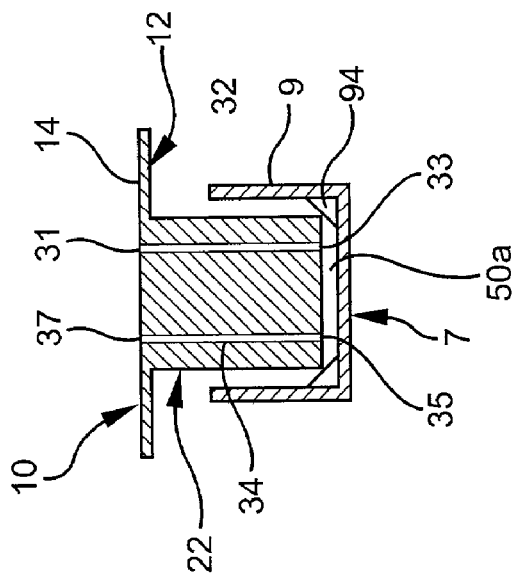
FIG. 15D shows the remote surface of a microcolumn resting on a flange for maintaining a capillary space between the remote surface and the bottom surface of a micro-titer well.
Figure 15C:
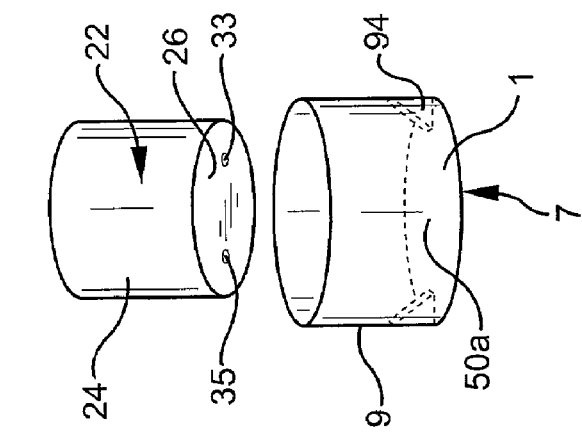

Various means can be used to maintain a constant capillary space 50a between the remote surface of a microcolumn 22 and the opposing bottom surface wall 7 of a micro-titer well 1. For instance, in alternate embodiments, a set of spacer elements 90 such as depicted in FIG. 14, on the remote surface of the microcolumn. The spacers 90 extend either from the remote surface 26 in an orthogonal orientation relative to the plane of the top surface, or (not shown) from a side surface 24. In an alternate arrangement and embodiment, spacers also can take the form of hemispherical beads, located equidistant to each other near the edge where the remote surface meets the side surface of the microcolumn. Also envisioned is a protruding, continuous ridge or bead that runs along the periphery of the remote surface.

Alternatively, as shown in FIG. 15, other kinds of spacer elements placed along the periphery of the bottom surface 7 of the well can be used to maintain a constant distance for the capillary space or gap 50a between the two opposing surfaces 7, 26. These spacers may be either a raised rib 92 or a flange 94, as illustrated in FIGS. 15A, 15B, and 15C, placed along the circumference of the bottom wall 7 where the bottom meets a sidewall 9 of the microplate well 1. As seen in FIGS. 15B and 15C, the flange 94 extends towards the center of the well 1 from its sidewall 9. The flanges 94 can be shaped as either a step (FIG. 15B), a triangle (FIG. 15C), a quarter circle such as of a bead or dowel (not shown), or any other shape. As seen in cross-section in FIG. 15D, the edge of the remote surface 26 rests against the flange 94. According to these embodiments, the height of the spacer, rib or flange determines the distance (capillary space 50a) of separation between the remote surface 26 and the well's bottom surface 7.

A pressure gradient or suction can propel the assay mixture up and down. The movement promotes microfluidic mixing during nucleic acid hybridization and incubation. This ability to mix the reaction either continuously or periodically may provide for greater improved assay kinetics, particularly for array-based assays, such as microarray hybridization applications. After incubation, wash steps can be performed within the present invention without disassemble it by injecting wash solutions through the inlets. The ability to perform continuous flow-through fluidics allows this device to be used for ligand binding kinetic studies and other real-time assay applications. The fluidic device may be used in conjunction with other equipment to perform both single and multiple target detection. Other potential array applications based on the present flow-through device include, in part: cDNA arrays for RNA expression profiling, oligonucleotide array for SNP scoring and RNA expression profiling, protein array, antibody array for protein profiling or solid phase ELISA, or chemical array for pharmaceutical screening, etc.

To test the efficacy of the present fluidic device, nucleic acid (DNA) arrays were prepared using polymerase-chain-reaction (PCR) amplified human gene sequences. FIG. 12 shows in comparison a representative array from each group. The assay using the array on the left hybridized under conventional static fluidic conditions. The assay using the array on the right was performed with fluidic movement according to the present invention. For each set of arrays, the inventors prepared about 2 μg total RNA, labeled with either Cy3 or Cy5 fluorescent dye, in 15 μL of total assay solution and allowed each array to hybridize for about four hours. A hybridization mixture or assay solution was prepared containing 6.25 μL of hybridization buffer (70% formamide, 3× SSC, and 14.3% dextran sulfate), 0.15 μL of 10% SDS, 1.5 μL of human Cot-1 DNA, 0.25 μL of Poly A (10 μg/μl), 1.5 μL of 2% BSA and 5.35 μL of labeled probes.

For each assay performed without fluidic movement, we placed about 9 μL of the hybridization mixture into a well printed with a test array, then inserted a microcolumn. The asembly was then incubated at 42° C. for 4 hours. For hybridization performed with fluidic movement, a fluidic device was first inserted. About 6 μL of the assay solution was injected through a microfluidic channel for each array in the second group and about 3 μL was used for fluidic movement back and forth, at a flow rate of 10 μL/min. during a 4-hour incubation at 42° C. Following hybridization the arrays were washed to remove non-hybridized probes, dried, and scanned.

Comparative hybridization results of the two examples are summarized in the accompanying graphs A-D of FIG. 13, which show the ratio of fluorence signal of the assay with fluidic movement over that of the assay without fluidic movement. The x-axis represents each spot on the array, and the y-axis is presented in logarithmic scale. A ratio of 1 signifies approximately equivalent performance in hybridization efficiency. The hybridization performed with a microfluidic device of the present invention can achieve a significant increase in hybridization efficiency, as reflected in the improved, overall signal of the array. Fluidic movement increases hybridization kinetics and corresponding signal. Additionally, one may use a diluted sample of probes combined with the fluidic movement to attain similar hybridization efficiency relative to non-diluted assays without fluidic movement. This feature provide advantageous cost savings when running assays.

Recent developments in the field of microarray technology suggest that porous surfaces for DNA microarrays can improve the signal to noise ratio. The developments indicate that porous surfaces yield an increase in hybridization signal intensity, but requires longer washings. A porous microarray surface, such as fabricated from a glass-fritted disc (e.g., aluminoborosilicates, borosilicates, Pyrex® or Vycor® by Corning Inc.), may provide dramatically improved hybridization efficiency because fluids can flow through the substrate. The hybridization solution passes back and forth through the porous surface, essentially eliminating the diffusion limitation of conventional hybridization processes. In addition, the flow-through nature of the glass disc will allow efficient washing of the array, leading to lower background signal.

FIG. 9 depicts a schematic of a fritted disc 70 being installed on the top of a microcolumn 22 housing, which can be made by injection molding. Also shown is a view of a cross-section of the microcolumn 22 and porous substrate 70 as inserted in a well 1. The different pore sizes can be chosen depending on the applications. For example, a fine pore size can be used for the flow-through array, while a bigger pore size can be used for the filtration and single or multiple capture purification. An array of selected biological molecules such as DNA or protein can be printed on the top surface of the porous disc by conventional contact printing or pieozo-electric ink-jet printing. Different surface chemistries will be built on the glass surface according to array materials. A non-covalent chemistry such as on aminated surfaces can be prepared with silane chemistry on the glass surface using a coating of, for instance, γ-aminopropyl-trimethoxysilane (GAPS) or polylycine. Covalent attachment mechanisms can also be introduced onto the porous substrate with epoxy, anhydride or N-hydroxysucciimide (NHS) chemistries.

As described before, to create movement of the assay solution through the porous substrate array, a pressure gradient or, as mentioned before, pipettes or syringes, or tubing attached by male luer adapters can be used to inject samples through the inlet to the remote major surface or into the reaction chamber. A pressure gradient also can be generated through a pipette (either a manual or robotic pipetting system) to be inserted into the inlet portal in the microcolumn. Drawing the fluid up and down with a pipette 11 mixes the solution and forces the liquid through the porous substrate 70 and over the array 5, as shown FIG. 10, forming essentially a mini hybridization chamber 51 in each well 1. This device can be easily built into a 96-microcolumn format, as illustrated in FIG. 11, to conform to currently robotic equipment systems.

Figure 6A:
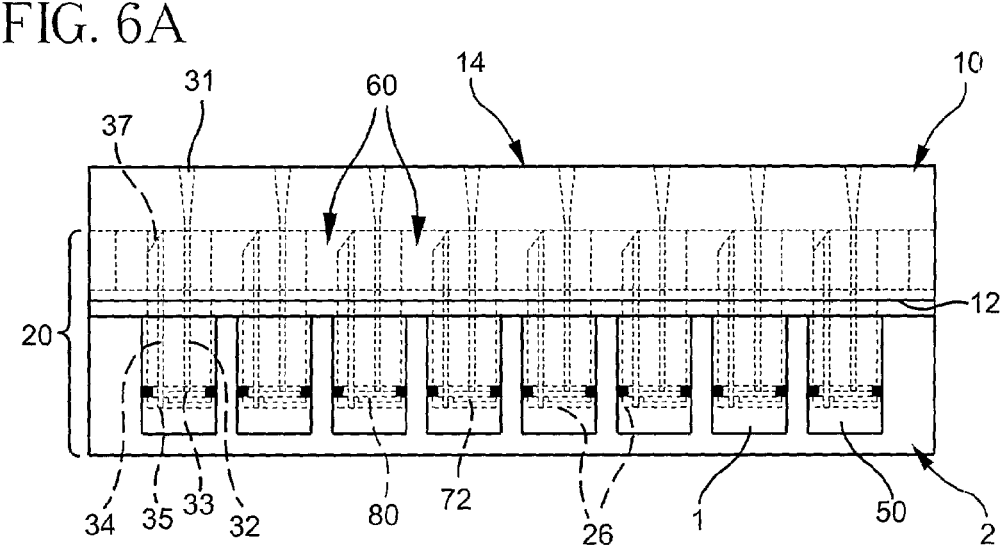
FIG. 6A is a diagram where the top of the microcolumn is integrated with a filter system for sample preparation.
Figure 6B:
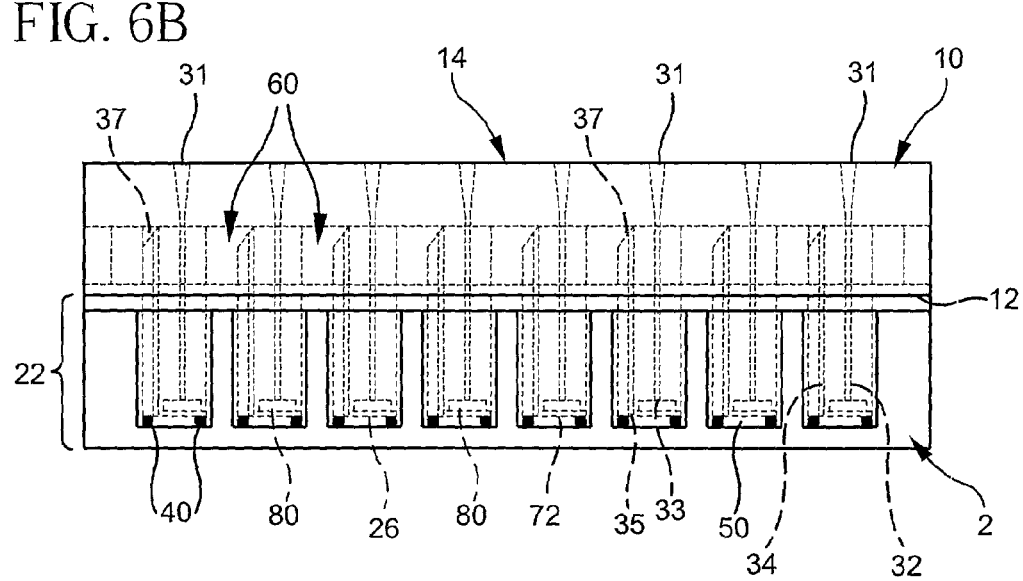
FIG. 6B is a diagram of an alternative design for the filter microcolumn depicted in FIG. 6A.
Figure 6C:
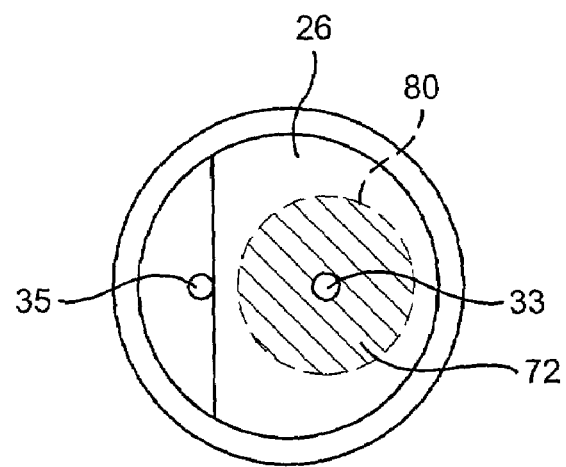
FIGS. 6C and 6D are head-on, enlarged views of the remote surfaces on the microcolumns in FIGS. 6A and 6B, respectively.
Figure 6D:
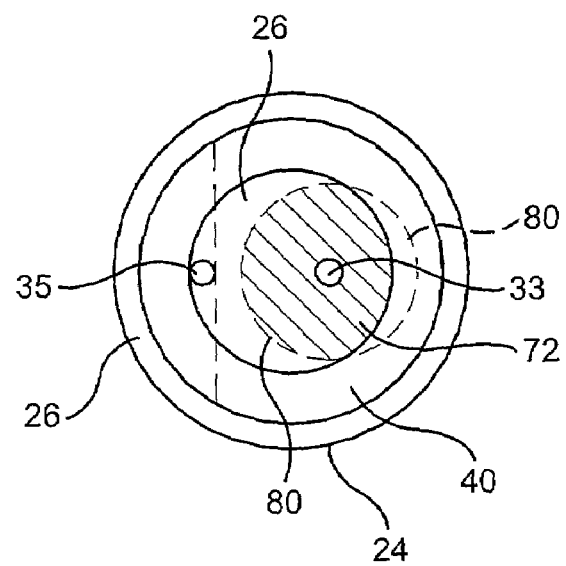

In a further embodiment, so as to be able to incorporate a porous substrate, membrane, or other filter, the top or remote major surface 26 of the microcolumn 22 may have a recess 80, like that shown in FIGS. 6A and 6B. The recess is larger than the cross-section of a microfluidic channel inlet or outlet port 33, 35. At least a part of the remote major surface 26 can be a filter 72. FIGS. 6C and 6D depict head-on, enlarged views of the major surface 26 of a microcolumn 22 from each of the devices depicted in FIGS. 6A and 6B, respectively. According to the example depicted in FIGS. 6A and 6B, fluids or solution samples are delivered through a first fluidic channel 32 and directed through the membrane 72 to filter or purify samples. A second fluidic channel 34 is positioned adjacent to the side of the filter for waste removal. The filter does not cover the inlet of the second fluid channel. Filter membranes could include commercially available membranes (e.g., nylon, cellulose acetate or cellulose nitrate), inorganic substrates (e.g., microporous glass or glass-frit wafer), or polymers and plastic (e.g., polystyrene, polyethylene, polyproplyene, polycarbonates, polyethylene terephthalate (PET), polysulfones, polyesters, or cyclic olefins). As opposed to a conventional flat membrane, the filter may also take a rigid, three-dimensional form of microporous plastic, similar to that described in U.S. patent application Ser. No. 09/591,892.

A fluidic module with a filter can be used for various applications that involve either high-throughput or continuous flow-through. Potential applications for high throughput sample preparations may include: PCR-product, DNA or RNA purification; specific protein capture using antibody-linked membranes; protein digest sample clean-up by C18 surface, Poly-A capture for mRNA purification, Protein A capture for antibody purification, or specific antibody for protein purification, protein sample clean-up or purification using chromatography (reverse phase, ion exchange, etc.); sample desalting, etc.

In general, the fluidic modules may be manufactured at a relatively low cost, such as mentioned above by injection molding of polymer materials. Metals such as gold can be vapor deposited onto the top of the microcolumns, which will allow attachment of biological molecules like DNA, peptides, proteins, etc., onto the gold surface through self assembled monolayer. The biological applications of the present invention may be similar to those described in U.S. Provisional Patent Application No. 60/317,660. According to other embodiments, the present invention may contain an electrochemical sensor, which may be inserted through a hollow conduit into the reaction chamber.

Figure 8:
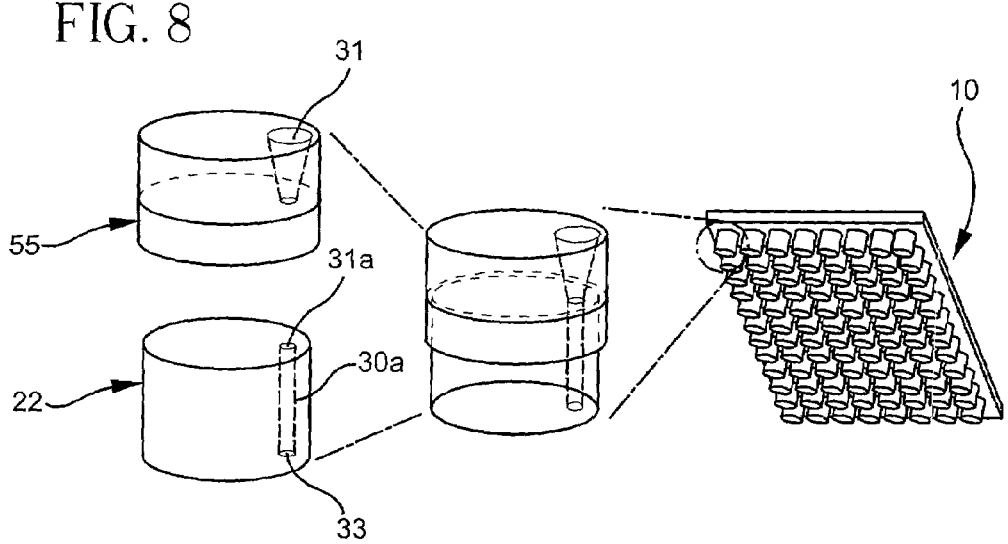
FIG. 8 shows another variation of the present invention, comprising a microcolumn plate with exchangeable hollow microcolumn-inserts of glass or polymer materials. A cap with an inlet port is aligned with the microchannel in the microcolumn.

FIG. 8 depicts an alternate, modular approach for assembling individual microcolumns to a plate. The figure shows a plate 10 with exchangeable hollow microcolumn-inserts 22 of glass or polymer materials, each with a detachable cap 55 having an inlet port 31, which is aligned with the microchannel 30a in the microcolumn 22. Modular variation allows individual microcolumns to be replaced or exchanged, or in case those areas become damaged, which presents a cost-effective advantage, as well as a single device that can be modified to meet various specifications for different applications.

In another aspect, the present invention includes a method of using an array of fluidic modules like that described above. The method comprises providing fluidic modules each with a set of at least one fluidic microchannel formed in a three-dimensional body. An inlet located in a surface of a support structure and extends through the support structure to the remote major surface of the module. Next, provide analytes on either the major surface of each module or the bottom surface of a well in a microplate, or both. Invert the device and insert the fluidic module into a corresponding well of the microplate, and introduce an assay medium through the inlet into the first fluidic microchannel. Create a reaction chamber or zone between the major surface of the module and the bottom surface of the well. The reaction zone has controlled fluid-flow direction. Introduce assay fluids into the well. The amount of assay mixture required to fill the assay reaction chamber can be adjusted by changing the gap distance (e.g., ~5 microns to ~5 mm) between the bottom of the well and the top of the microcolumns. Preferably present is a second microfluidic channel, which extends at least partially through the support structure or the body of the fluidic module from the remote major surface an outlet port, to permit reaction medium to exit through after interaction with the analytes. As mentioned before, assay fluids can be pumped continuously, either forwards or backwards, through the device to the reaction chamber.

Also as part of the invention, the inventors envision a kit for high-throughput biological or chemical assays. The kit includes a fluidic device, according to the present invention, and a well plate having in each well a bottom wall with a depression around the center of the bottom for receiving fluids and acting as a reaction chamber once corresponding microcolumns are secured against the plate. The kit may also have grating structures for biosensing uses.

The present invention has been described in detail by way of examples. Persons skilled in the art, however, may appreciate that modifications and variations may be made to the present device without departing from the scope of the invention, as defined by the appended claims and their equivalents.

We claim:

1. A fluidic device for performing high-throughput biological or chemical assays, the device comprising:
    a support structure with a first surface and a second surface;
    a number of microcolumns extending from said first surface;
    each of said microcolumns having a first and a second fluidic channel formed therein and a planar, major surface remotely located relative to said first surface;
    said first fluidic channel having an inlet port and extending through said microcolumn from said second surface of said support structure through said remote planar, major surface;
    said second fluidic channel extending at least partially through said microcolumn from said remote planar, major surface to an outlet portal; and
    a microplate having a plurality of wells wherein each microcolumn is sized so as to be introduced into the corresponding well of said microplate;
    wherein each of said microcolumns has a sealing mechanism that engages with a bottom wall of said well to form a fluid-tight space.

2. The fluidic device according to claim 1, wherein said microcolumn is positioned into said microplate a predetermined distance above a bottom wall of said corresponding well.

3. The fluidic device according to claim 1, wherein said sealing mechanism is a gasket, an O-ring, a rib or flange on a distal surface.

4. The fluidic device according to claim 1, wherein said microcolumns are arrayed in a matrix.

5. The fluidic device according to claim 4, wherein said matrix is in a 24-, 48-, 96-, 192, 384, or 576-well format.

6. The fluidic device according to claim 1, wherein said microcolumns are arrayed on a strip.

7. The fluidic device according to claim 6, wherein said strip is in a 6, 8, 12 well format.

8. The fluidic device according to claim 1, wherein said first and second fluidic channels enable continuous flow of fluids in through said first fluidic channel into a reaction chamber and out through said second fluidic channel.

9. The fluidic device according to claim 1, wherein at least a part of said remote planar, major surface of said microcolumn is configured with a porous substrate.

10. The fluidic device according to claim 9, wherein said porous substrate is a membrane, filter, polymer, or glass-frit wafer.

11. The fluidic device according to claim 1, wherein said remote planar, major surface of said microcolumn has a recess that is larger than the cross-section of a first fluidic channel.

12. The fluidic device according to claim 1, wherein said inlet port is sized to permit a pipette tip, syringe, or other conduit to be introduced within.

13. The fluidic device according to claim 1, wherein when said second fluidic channel extends to an outlet port on a second planar surface, said outlet port is configured to receive a conduit for fluids.

14. The fluidic device according to claim 1, wherein an array of biological or chemical analytes is disposed on said remote planar, major surface.

15. The fluidic device according to claim 14, wherein said biological analytes include DNA, RNA, proteins, cells, and cellular components.

16. The fluidic device according to claim 1, wherein said device further includes an electrochemical sensor.

17. The fluidic device according to claim 1, wherein said device further comprises an optical detection device for monitoring assays.

18. A fluidic device for performing high-throughput biological or chemical assays, the device comprising:
    a support structure with a first surface and a second surface;
    a number of microcolumns extending from said first surface;
    each of said microcolumns having a first and a second fluidic channel formed therein and a major surface remotely located relative to said first surface;
    said first fluidic channel having an inlet port and extending through said microcolumn from said second surface of said support structure through said remote major surface;
    said second fluidic channel extending at least partially through said microcolumn from said remote major surface to an outlet portal, wherein said outlet portal exits into waste passages located in said support structure; and a microplate having a plurality of wells wherein each microcolumn is sized so as to be introduced into the corresponding well of said microplate;

wherein each of said microcolumns has a sealing mechanism that engages with a bottom wall of said well to form a fluid-tight space.

19. The fluidic device according to claim 18, wherein said waste passages form a common reservoir.

20. A fluidic device for performing high-throughput biological or chemical assays, the device comprising:

a support structure with a first surface and a second surface;

a number of microcolumns extending from said first surface;

each of said microcolumns having a first and a second fluidic channel formed therein and a major surface remotely located relative to said first surface;

said first fluidic channel having an inlet port and extending through said microcolumn from said second surface of said support structure through said remote major surface;

said second fluidic channel extending at least partially through said microcolumn from said remote major surface to an outlet portal, wherein said outlet portal exits onto said second surface of said support structure; and a microplate having a plurality of wells wherein each microcolumn is sized so as to be introduced into the corresponding well of said microplate;

wherein each of said microcolumns has a sealing mechanism that engages with a bottom wall of said well to form a fluid-tight space.

* * * * *